United States Patent
Susak et al.

(10) Patent No.: US 8,894,982 B2
(45) Date of Patent: Nov. 25, 2014

(54) MOISTURIZING COMPOSITIONS FOR LIP

(75) Inventors: Milanka Susak, North York (CA); John R. Castro, Huntington Station, NY (US); Isaac David Cohen, Brooklyn, NY (US)

(73) Assignee: ELC Management, LLC, New York, NY (US)

( * ) Notice: Subject to any disclaimer, the term of this patent is extended or adjusted under 35 U.S.C. 154(b) by 263 days.

(21) Appl. No.: 12/952,624

(22) Filed: Nov. 23, 2010

(65) Prior Publication Data

US 2012/0129956 A1    May 24, 2012

(51) Int. Cl.
| | | |
|---|---|---|
| *A61K 8/00* | (2006.01) | |
| *A61Q 5/12* | (2006.01) | |
| *A61Q 19/00* | (2006.01) | |
| *A61K 8/06* | (2006.01) | |
| *A61K 8/37* | (2006.01) | |
| *A61K 8/891* | (2006.01) | |

(52) U.S. Cl.
CPC ............. *A61Q 19/001* (2013.01); *A61K 8/064* (2013.01); *A61K 8/37* (2013.01); *A61K 8/375* (2013.01); *A61K 8/891* (2013.01)
USPC .......................................... 424/64; 424/70.12

(58) Field of Classification Search
None
See application file for complete search history.

(56) References Cited

U.S. PATENT DOCUMENTS

| | | | |
|---|---|---|---|
| 4,226,889 A | 10/1980 | Yuhas | |
| 4,322,400 A | 3/1982 | Yuhas | |
| 4,507,279 A | 3/1985 | Okuyama et al. | |
| 5,197,814 A | 3/1993 | Lombardi et al. | |
| 5,310,547 A | 5/1994 | Dunphy et al. | |
| 5,466,457 A | 11/1995 | Schneider et al. | |
| 5,645,903 A | 7/1997 | Tanaka et al. | |
| 6,162,421 A | 12/2000 | Ordino et al. | |
| 7,083,800 B1 | 8/2006 | Terren et al. | |
| 2007/0166247 A1 | 7/2007 | Aliano et al. | |
| 2009/0035242 A1* | 2/2009 | Maes et al. | 424/64 |
| 2009/0074822 A1 | 3/2009 | Declercq et al. | |
| 2009/0155371 A1* | 6/2009 | Sojka et al. | 424/497 |
| 2012/0156271 A1* | 6/2012 | Matsuzawa et al. | 424/401 |

FOREIGN PATENT DOCUMENTS

| | | |
|---|---|---|
| JP | 2001-348310 | 12/2001 |
| JP | 2004-203788 | 7/2004 |
| JP | 2005-225806 | 8/2005 |
| WO | WO-2009/017866 | 2/2009 |
| WO | WO-2009/082511 | 7/2009 |
| WO | WO-2009/105294 | 8/2009 |

OTHER PUBLICATIONS http://www.gnpd.com; Mintel gnpd; Record ID: 280062; Lancome; Primordiale Optimum Levres Lip Treatment; Skincare; Lipcare; Italy; Jun. 2004.
"Tospearl 150KA Microspheres, New micro-spherical silicone powder with spiky surface," Momentive Performance Materials; pp. 1-8; 113-810-00E-GL, Jan. 2008.
"Water Resistance" in "Formulating for Sun;" Publisher, Allured Pub. Corp., Feb. 1, 2006.
PCT International Search Report; International Application No. PCT/US2011/059296; Completion Date: Jun. 18, 2012; Mailing Date: Jun. 20, 2012.
PCT Written Opinion of the International Searching Authority; International Application No. PCT/US2011/059296; Completion Date: Jun. 18, 2012; Mailing Date: Jun. 20, 2012.

* cited by examiner

*Primary Examiner* — Lezah Roberts
*Assistant Examiner* — Nannette Holloman
(74) *Attorney, Agent, or Firm* — Julie M. Blackburn

(57) ABSTRACT

A water in oil emulsion lip treatment composition comprising at least one non-polar silicone oil, at least one non-polar organic oil, at least one amphiphilic organic emollient oil, at least one water in oil surfactant; and at least one oil in water surfactant.

7 Claims, No Drawings

MOISTURIZING COMPOSITIONS FOR LIP

TECHNICAL FIELD

The invention is in the field of compositions and methods for treating lips.

BACKGROUND OF THE INVENTION

One common complaint from consumers is that colored lip products may sometimes be drying on the lips. This is often the case when lip products contain significant amounts of pigments and powders to provide the desired color. These types of particulates can be drying on the lips. Water is believed to be the ultimate hydrator. Paradoxically, however, lip products formulated with water can be even more drying to the lips than their anhydrous counterparts. The reason for this is that water is a fairly fast drying solvent. While the water-containing lip product will provide an immediate feel of hydration when the product is applied to the lips, the water evaporates quickly. Consumers report that the lips are left feeling dryer than before the application of product.

Cosmetic formulators are constantly searching for ways to formulate water containing lip products that are as moisturizing as their standard anhydrous counterparts and the lip products commonly sold for lip treatment purposes. Water containing lipsticks that have some degree of water resistance and occlusiveness are most beneficial for creating a moisturizing film on the lips with a water based lipstick. That is, the film forming ingredients present in the composition must provide a film that will hold the water and inhibit its immediate evaporation from the film surface. In this case the water present is able to hydrate the lip. Some of the reasons a film may become disrupted include re-emulsification of the film, removal by mechanical action, or when the active (water) is not well entrapped within the film.

It has been most unexpectedly discovered that a water containing lip product having non polar oils, amphiphilic oils, and both types of surfactants (e.g. water in oil and oil in water) provide an excellent lip product that contains significant amounts of water and yet provides moisturization properties equivalent to, or better than products sold specifically for moisturizing lips.

SUMMARY OF THE INVENTION

The invention is directed to a water in oil emulsion lip composition comprising at least one non-polar silicone oil, at least one non-polar organic oil, at least one amphiphilic organic emollient oil, at least one water in oil surfactant; and at least one oil in water surfactant.

The invention is further directed to a method for moisturizing and hydrating lips by applying a composition comprising at least one non-polar silicone oil, at least one non-polar organic oil, at least one amphiphilic organic emollient oil, at least one water in oil surfactant; and at least one oil in water surfactant.

DETAILED DESCRIPTION

The composition of the invention is in the form of a water in oil emulsion. The composition may contain from about 0.1 to 95%, preferably 1-85%, more preferably from about 5-75% water. (All percentages referred to herein are percentages by weight unless otherwise indicated). The composition will contain from about 0.1-99% oil, preferably from about 1-85%, and more preferably from about 2-50%

The Non-Polar Silicone Oil

The composition contains at least one non-polar silicone oil. The term "oil" means that the ingredient referred to is a pourable liquid at room temperature (e.g. 25° C.). The silicone oil may be volatile or non-volatile. The non-polar silicone oil may be present ranging from about 0.1 to 85%, preferably from about 1-75%, more preferably from about 2-65%.

Examples of volatile silicones include linear, cyclic, or branched volatile silicones such as cyclopentasiloxane, cyclohexasiloxane, hexamethyldisiloxane, octamethyltrisiloxane, decamethyltetrasiloxane, dodecamethylpentasiloxane, methyl trimethicone, and the like.

Suitable non-volatile silicone oils include dimethicone, phenyl trimethicone diphenyl dimethicone, trimethylsiloxyphenyl dimethicone, cetyl dimethicone, and the like.

Preferred is where the non-polar silicone oil comprises at least one volatile silicone and at least one non-volatile silicone. More preferred is where the non-polar silicone oil comprises methyl trimethicone (having viscosity of about 1.5 centistokes—cst) and dimethicone having a viscosity ranging from about 50 to 500 cst).

The Non-Polar Organic Oil

The lip product of the invention comprises at least one non-polar organic oil which is pourable at room temperature. Such oil may be present ranging from about 0.1 to 80%, preferably from about 0.5 to 75%, more preferably from about 1 to 70%. Examples of non-polar organic oils include mono-, di-, or triesters of aliphatic or aromatic carboxylic acids and alcohols. Examples of such esters include esters of aliphatic or aromatic alcohols, for example having from about 2 to 40 carbon atoms, and aliphatic or aromatic C2-40 carboxylic acids, such as C1-10 carboxylic acid esters of C12-20 fatty alcohols such as stearyl, behenyl, isostearyl, cetyl, and so on. More preferred are non-polar organic oils that have a viscosity ranging from about 10 to 400 cst at room temperature.

Further specific examples include esters of short chain carboxylic acids and fatty alcohols such as C1-8 carboxylic acids which may be substituted with hydroxyl groups and C10-22 fatty acids. Examples of C1-4 carboxylic acids include citric acid, malic acid, lactic acid, propionic acid, butyric acid, caprylic acid, caproic acid, and so forth. Fatty alcohols include stearyl, cetearyl, cetyl, linoleyl, and so on. Further specific examples of such esters include but are not limited to triisostearyl citrate, tricaprylin, diisostearyl malate, cetearyl olivate, and so on.

The Amphiphilic Organic Oil

The composition will also contain at least one amphiphilic organic oil. The term "amphiphilic" means that the oil has polar and non-polar portions. The amphiphilic oil is present ranging from about 0.1 to 70%, preferably from about 0.5 to 65%, more preferably from about 1 to 50%.

Examples of amphiphilic oils include those that are substituted with mono, di, orpolyhydroxy alcohols, glycerol or polyglycols, pentaerythritol, and so on. Specific examples include, but are not limited to, neopentyl glycol diheptanoate, bis-diglyceryl polyacyladipate, caprylic/capric triglyceride, dipentaerythrityl tri-polyhydroxystearate, glyceryl behenate/eicosadioate, oleic/linoleic/linolenic polyglyceride, PEG-30 dipolyhydroxystearate, and so on.

The Water in Oil Surfactant

The composition also contains at least one water in oil surfactant. Preferred ranges are from about 0.1 to 75%, preferably from about 0.5 to 70%, preferably from about 1 to 60%. The term "water in oil surfactant" means a nonionic surfactant that preferably has a hydrophile lipophile balance ranging from about 4 to 6. The surfactants may be organic or silicone based. Preferably, in a preferred embodiment, the water in oil surfactant is silicone based. More preferred is a water in oil silicone surfactant generically referred to as an alkyl dimethicone copolyol. Specific examples include alkyl substituted dimethicone copolyols such as cetyl dimethicone copolyol or other alkyl substituted dimethicone copolyols where the alkyl chain provides a lipophilic property. Cetyl dimethicone copolyol may be more specifically referred to by enumerating the number of repeating EO (ethylene oxide) or PO (propylene oxide) groups, for example: Cetyl PEG/PPG-10/1 dimethicone. Also suitable is PEG-30 dipolyhydroxystearate.

Oil in Water Surfactant

The composition comprises at least one oil in water surfactant, preferably present in an amount ranging from about 0.01 to 80%, preferably from about 0.05 to 75%, more preferably from about 0.1 to 70%. Such oil in water surfactant is preferably one or more nonionic organic surfactants. Further examples include sorbitan derivatives such as sorbitan stearate, sorbitan triisostearate, sorbitan olivate, sorbitan oleate, sorbitan sesquioleate, PEG derivatives thereof such as PEG 2-300 (from 2 to 300 ethylene glycol repeat units) sorbitan derivatives.

Other Ingredients

Waxes

The composition preferably contains one or more waxes. The term "wax" means an ingredient that is solid or semi-solid at room temperature, having a melting point ranging from 30 to 120° C. If present such waxes may range from about 0.001 to 70%, preferably from about 0.005 to 65%, more preferably from about 0.01 to 60% of the composition. Such waxes include fatty alcohols such as behenyl alcohol, stearyl alcohol, linoleyl alcohol, and the like. Also suitable are animal, vegetable or mineral waxes including beeswax, synthetic wax, plant derived waxes like astrocaryum murumuru seed butter, sunflower seed wax, bayberry wax, and the like.

Thickening Agents

The composition may contain one or more aqueous based thickening agents. If present, suggested ranges are from about 0.01-40%, preferably from about 0.05-35%, more preferably from about 0.1-30%. Examples of suitable aqueous based thickening agents include xanthan gum, acrylate based polymers such as carbopol, dimethyltaurate based acrylic polymers, and the like.

Pigments and Particulates

If desired the lip composition may be pigmented. Suggested ranges of particulates may be from about 0.1 to 70%, preferably from about 0.5 to 65%, more preferably from about 1 to 50%. Suitable pigments include organic and inorganic pigments such as the D&C and FD&C colors or iron oxides such as red, yellow, black, iron oxides. Also suitable are non-pigmented particulates that may be white or colorless, more commonly referred to as powders. Examples include nylon, PMMA, titanium dioxide, zinc oxide, and the like.

Humectants

It may be desirable to include one or more humectants in the composition. If present, suggested ranges are from about 0.01 to 20%, preferably from about 0.05 to 15%, more preferably from about 0.1 to 10%. Examples of humectants include mono-, di, or polyhydric alcohols such as glycerol, butylene glycol, propylene glycol, pentane diol, and so on.

The invention will be further described in connection with the following examples which are set forth for the purposes of illustration only.

Example 1

A water containing lip product in accordance with the invention was made as follows:

| Ingredient | % by weight |
| --- | --- |
| Water | QS100 |
| Triisostearyl citrate | 9.50 |
| Neopentyl glycol diheptanoate | 7.00 |
| Tricaprylin | 6.00 |
| Beeswax | 5.50 |
| Bis-diglyceryl polyacyladipate | 4.80 |
| Dimethicone | 4.50 |
| Glycerin | 4.00 |
| Sunflower seed wax | 3.00 |
| Methyl trimethicone | 2.50 |
| Caprylic/capric triglyceride/stearalkonium hectorite/propylene carbonate | 2.00 |
| Diisostearyl malate | 2.00 |
| Dipentaerythrityl tri-polyhydroxystearate | 2.00 |
| Behenyl alcohol | 1.75 |
| Cetyl PEG/PPG-10/1 dimethicone | 1.75 |
| Glyceryl behenate/eicosadioate | 1.50 |
| Oleic/linoleic/linolenic polyglyceride | 1.50 |
| PEG-30 dipolyhydroxystearate | 1.00 |
| *Astrocaryum murumuru* seed butter | 1.00 |
| Water/glucose/*Laminaria digitata* extract | 0.70 |
| Cetearyl olivate/sorbitan olivate | 0.50 |
| Xanthan gum | 0.25 |
| Tocopherol acetate | 0.20 |
| Potassium sorbate | 0.05 |
| Water/glucose oxidase/lactoperoxidase | 0.04 |

The water phase ingredients except for xanthan gum were combined and heated to 65° C. The xanthan gum was then added to the water phase and mixed for about 30 minutes until dissolved. The glycerin was added to the water phase mixture. The oil phase ingredients were combined separately in a vessel and heated to 65° C. until completely melted. The two phases were combined with high speed propeller mixing. The composition was cooled to 40° C. The preservatives were added with sweep mixing. The composition was cooled to 30° C. and poured into containers.

Example 2

Various lip products were selected and/or prepared for comparative clinical testing, as follows: lip compositions A, B, C, D, and E were comparatively tested for moisturizing properties. Product A was petrolatum. Product B was the commercial product Clinique Repair Wear Intensive Lip Treatment. The ingredient list on the package is set forth below:

Octyldodecanol, pentaerythrityl adipate/caprate/caprylate/heptanoate, petrolatum, bis-diglyceryl polyacyladipate-2, polyethylene, hydrogenated dilinoleyl alcohol, stearoxy dimethicone, silica, polybutene, microcrystalline wax (cera microcristillina), water purified, *triticum vulgare* germ extract, *polygonum cuspidatum* root extract, *theobroma grandiflorum* seed butter, *mentha piperita, coffea arabica* seed extract, *rosmarinus officinalis* extract, tocopheryl acetate, *coffea robusta* seed extract, *betula alba* extract, astrocaryum murumuru butter, *hordeum vulgare* extract, *butyrospermum parkii,* glycerin, *poria cocos* sclerotium extract, linolenic acid, sodium DNA, *saccharomyces* lysate extract, linoleic acid, cholesterol, sodium RNA, ascorbyl tocopheryl maleate, methyl glucose sequistearate, lauryl PCA, C20-40 pareth-10, squalane, ethylhexyl glycerin, polyglyceryl-4 isostearate, hexyl laurate, cetyl PEG/PPG-10/1 dimethicone, allyl methacrylates crosspolymer, propylene glycol dicaprate, nordihydroguaiaretic acid, glycine soja (soybean) protein, phytosphingosine, phospholids, oleic acid, acetyl carnitine HCL, caprylic/capric triglyceride, triethoxycaprylsilane, ethyl hexyl stearate, ethyl hexyl palmitate, potassium sulfate, hydroxyethylcellulose, ethylcellulose, BHT, phenoxyethanol (+/− may contain: mica, red 7 lake (CI 15850), yellow 5 lake (CI 19140), red 22 lake (CI 45380), red 30 lake (CI 73360), carmine (CI 75470), red 33 lake (CI 17200), red 28 lake (CI 45410), titanium dioxide (CI 77891), iron oxides (CI 77491, CI 77492, CI 77499), red 6 (CI 15850), blue 1 lake (CI 42090), yellow 6 lake (CI 15985)

Product C was a trade name mixture of ingredients called Probiol NO3068 DMS—Ceramide Enriched, containing water, sodium PCA, Glycine, Squalane, Hydrogenated Lecithin, Pentylene glycol, Ceramide 3, Glycerin, Serine, Alanine Product D was the commercial product Lancome Primodiale Optimum Levres Lip Treatment. The ingredient list set forth on the package read as follows:

Aqua/water, cyclopentasiloxane, hydrogenated polyisobutene, dimethicone/vinyl dimethicone crosspolymer, dimethicone, glycerin, nylon-12, microcristallina/microcrystalline wax, phenyl trimethicone, prunus armeniaca/apricot kernel oil, ethylene/acrylic acid copolymer, silica, dimethicone copolyol, polysorbate 20, tocopheryl acetate, tocopherol magnesium sulfate, *fagus sylvatica/fagus sylvatica* extract, glycine soja/soybean oil, octyl methoxycinnamate, imidazolidinyl urea, chorphenesin, polycaprolactone, propyl paraben, acrylates copolymer, methylparaben, CI77491, iron oxides (CI77492).

Product E was the formula set forth in Example 1 above.

Example 3

Women panelists from 19-76 years of age (mean age 48) received one of products A, C, and E. Prior to beginning the test, the lower lip of each panelist was measured to beginning skin hydration using a Corneometer® CM825, Courage & Khazaka. The Corneometer probe was placed perpendicularly onto the lip surface. The measurement of skin hydration, expressed as corneometer units, appeared on the screen. For each subject and reading, the measurements were repeated at least five times on different sites on the target surface but close in vicinity to each other. The measurements were repeated until the standard deviation of the last five measurements was less than 2. After the baseline reading was taken, the panelists were told to apply the test product four times per day for the next eight days, with one application two hours before visiting the clinical test center for corneometer hydration measurement. Hydration measurements were taken at 2 hours, 2 days, and 1 week after the first application. On the 8th day the lip product was discontinued. The panelists were asked to refrain from using any lip product for the next two days. On day 10, the panelists visited the test center for corneometer measurement of skin hydration. The baseline hydration readings were subtracted from the end result. The average of the results for each of the ten panelists were as follows:

| Product | Baseline | 2 hours | 2 days | 8 days | 10 days |
|---|---|---|---|---|---|
| A (petrolatum) | 41.69 | 65.95 | 61.78 | 64.03 | 54.76 |
| A (reading - baseline) | — | 24.26 | 20.09 | 22.34 | 13.07 |
| C (Probiol) | 59.24 | 86.38 | 83.35 | 76.19 | 60.26 |
| C (reading - baseline) | | 27.14 | 24.11 | 16.95 | 1.02 |
| E (Invention) | 45.12 | 58.06 | 63.69 | 66.09 | 51.95 |
| E (reading - baseline) | | 12.94 | 18.57 | 20.97 | 6.83 |

The above results demonstrate that when the composition of the invention is compared to lip hydration standards petrolatum and Probiol, both of which provide maximum hydration, but are not commercially acceptable from an aesthetic point of view, it surpasses other commercial products in the market. This is true even while the composition of the invention contains significant amounts of water.

Example 4

Women panelists from 19-76 years of age received one of products A, B, C, D, and E. Prior to beginning the test, the lower lip of each panelist was measured to beginning skin hydration using a Corneometer® CM825, Courage & Khazaka. The Corneometer probe was placed perpendicularly onto the lip surface. The measurement of skin hydration, expressed as corneometer units, appeared on the screen. For each subject and reading, the measurements were repeated at least five times on different sites on the target surface but close in vicinity to each other. The measurements were repeated until the standard deviation of the last five measurements was less than 2. After the baseline reading was taken, the panelists were told to apply the test product. Hydration measurements were taken at 1½, 3, and 6 hours after the first application. The baseline hydration readings were subtracted from the end result. The average of the results for the panelists were as follows:

| Product | 0 hours | 1.5 hours | 3 hours | 6 hours |
|---|---|---|---|---|
| A (Petrolatum) | 0 | 28.38 | 4.00 | 1.23 |
| B (Clinique Repairwear) | 0 | 13.43 | 7.26 | 2.45 |
| C (Probiol) | 0 | 31.80 | 17.38 | 14.52 |
| D (Lancôme Primordiale) | 0 | 17.93 | 9.82 | 8.90 |
| E (Invention) | 0 | 18.31 | 16.07 | 8.95 |

Both petrolatum (Product A) and Probiol (Product C) are benchmark formulas that provide an excellent hydration profile but are not aesthetically suitable for commercial sale as lip products. Accordingly, the objective was to formulate products that are aesthetically pleasing enough to be commercially acceptable and having a hydration profile that approximates those products that are benchmarks for same. The above results demonstrate that the composition of the invention exhibits the most hydration at 1.5, 3, and 6 hours. The long term hydration of the invention composition is better than Product A, petrolatum at 3 and 6 hours after application and close to benchmark Probiol at 3 hours after application.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:
1. A water in oil emulsion lip treatment composition comprising:
from about 0.1 to 85% of a nonpolar silicone oil comprising dimethicone having a viscosity ranging from about 100 to 500 cst and a volatile silicone;
from about 0.1 to 80% of a nonpolar organic oil comprising a mixture of triisostearyl citrate, and diisostearyl malate;
from about 0.1 to 70% of an amphiphilic organic oil comprising neopentyl glycol diheptanoate, bis-diglyceryl polyacyladipate, caprylic/capric triglyceride, dipen- taerythrityl tri-polyhydroxystearate, glyceryl behenate/ eicosadioate, oleic/linoleic/linolenic polyglyceride, PEG-30 dipolyhydroxystearate, or mixtures thereof;

from about 0.1 to 75% of a water in oil surfactant comprising an alkyl dimethicone copolyol; and from about 0.01 to 80% of an oil in water surfactant comprising sorbitan stearate, sorbitan triisostearate, sorbitan olivate, sorbitan oleate, sorbitan sesquioleate, or a PEG derivative thereof;

wherein said composition maintains sustained hydration for at least 3 hours after application to the lips; wherein the sustained hydration is measured with a corneometer in corneometer units and is at least 16.07 corneometer units when measured at 3 hours.

2. The composition of claim 1 wherein the amphiphilic organic oil comprises a mixture of triisostearyl citrate, diisostearyl malate, and cetearyl olivate.

3. The composition of claim 1 wherein the amphiphilic organic oil comprises a mixture of neopentyl glycol diheptanoate, bis-diglyceryl polyacyladipate, caprylic/capric triglyceride, dipentaerythrityl tri-polyhydroxystearate, oleic/linoleic/linolenic polyglyceride, and PEG-30 dipolyhydroxystearate.

4. The composition of claim 1 wherein the water in oil surfactant is cetyl PEG/PPG-10/1 dimethicone.

5. The composition of claim 1 wherein the oil in water surfactant comprises sorbitan olivate.

6. The composition of claim 1 further comprising at least one humectant which is glycerin.

7. The composition of claim 1 wherein the sustained hydration at 1.5 hours is at least 18.31 comeometer units.

* * * * *